US00PP09296P

United States Patent [19]

van Andel

[11] Patent Number: Plant 9,296

[45] Date of Patent: Sep. 19, 1995

[54] POT FREESIA VARIETY NAMED 'VAPONO'

[75] Inventor: Jacob van Andel, Aalsmeer, Netherlands

[73] Assignee: Van Staaveren B.V., Aalsmeer, Netherlands

[21] Appl. No.: 331,881

[22] Filed: Oct. 31, 1994

[51] Int. Cl.[6] ..... A01H 5/00

[52] U.S. Cl. ..... Plt./83

[58] Field of Search ..... Plt. 83

*Primary Examiner*—James R. Feyrer

*Attorney, Agent, or Firm*—Christie, Parker & Hale

[57] ABSTRACT

A new variety of pot freesia suitable for growing indoors as a potted plant.

1 Drawing Sheet

BACKGROUND OF THE INVENTION

This invention relates to a new and distinct variety of Freesia which originated by crossing two unpatented, unnamed varieties of my creation at the Van Staaveren b.v. Nursery in Aalsmeer, the Netherlands. The female parent is identified as 86327-AP1 and the male parent is identified as 87320-AP1. The varietal demoination of the new variety is VAPONO.

SUMMARY OF THE INVENTION

Among the features which distinguish the new variety from other presently available and known commercial cultivars are the following combination of characteristics: attractive pale yellow flowers, a habit of growth which distinguishes the new variety as a plant suitable for growing in pots and referred to as a pot freesia variety reflecting its natural dwarf characteristics without need of growth retardants, and its ability to flower independent of soil temperature up to about 23° C. in about 65 to about 90 days.

Asexual reproduction vegetatively by corms and cormlets in Aalsmeer, Netherlands shows that the foregoing and other distinguishing characteristics of the new variety are transmitted through succeeding generations.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this description, color values are based upon the Colour Chart of The Royal Horticultural Society of London, England, except where common terms of color definition are employed.

DESCRIPTION OF THE NEW VARIETY

The following description is of pot freesia plants of the new cultivar grown under glass in Aalsmeer, Netherlands, during the months of August and September. Phenotyphic expression may vary with environment, cultural and climatic conditions, as well as differences and conditions in light, soil, and temperature.

PLANT

A. Form: Upright.

B. Growth:

*Height attained.*—Depending on temperature, about 25 cm to about 35 cm The higher the temperature, the more leaves the plant produces and the longer they are at higher temperatures, the more buds are produced in a spike. The lower the light intensity the longer and weaker are the leaves. Each combination of temperature and light intensity has a special formative influence on plant shape. Measurements given herein were made on plants grown initially at 12° C. and up to 24° C. at flowering time. Generally, The cooler the plants are grown, the more compact the plants will grow and the more days that are necessary between planting and flowering.

*Branching.*—The flower stalk bears 1 or 2 short side shoots with flower buds.

C. Flower stem:

1. *Length.*—Depending on temperature, about 25 cm to about 35 cm.
2. *Color.*—Medium green, surface rough.

D. Foliage:

1. *Size.*—Length — about 25 to about 30 cm. Width — about 1 cm to about 3 cm depending on temperature and light during growth.
2. *Quantity.*—5-8 leaves depending on growing temperature.
3. *Shape of leaf.*—Oblong with entire margins.
4. *Texture.*—Smooth.
5. *Color.*—Near 146A to 146B.
6. *Veination.13* Freesia-like.
7. *Stem color.*—Near 16A.
8. *Corms.*—Color: White with brown scales. Size: Varying with age, circumference up to about 85 mm.

THE BUD STAGE

A. Bud form: Long ovate.

B. Bud side:

*Length.*—About 40 mm.

*Diameter.*—About 15 mm to about 20 mm.

C. Opening rate: Medium.

D. Color:

1. *When petals first divide.*—Near 4D with a green shade.
2. *When petals begin to unfurl.*—Near 4D.
3. *Calyx.*—Shape — tubular. Size — small, smooth.

THE FLOWER STAGE

A. Inflorescence:

1. *Blooming habit.*—Intermittent, once early.
2. *Form.*—Freesia-like.

3. *Approximate number of flowers.*—8 to 10 per spike.
4. *Borne.*—In a spike.
5. *Size.*—Diameter — about 45 mm. Depth — about 65 mm to about 75 mm.
6. *Shape.*—Cup shaped.
7. *Color tonality from a distance.*—Pale yellow.
8. *Lasting quality (days) on plant.*—About 12 to about 18 days depending on temperature.

B. Flower color:

1. *Flower coloration.*—Main color of inner side of the lateral outer tips, near 6D and near 23A; main color of inner side of the medium outer tips, near 6D and near 23A.
2. *Inner petals.*—Main color of inner side lateral inner tips, near 23A and near 6D.
3. Outer petals.—Main color of inner side of the medium inner tips near 6D.

4. *Discoloration as bloom ages.*—Flower color darkens to light brown.
5. *Petals.13* Number of petals: 6. Arrangement: Tubular, imbricated. Texture Soft. Shape 6 tips of the tube.

C. Persistence: Petals persist to about 12 to about 18 days on the plant.

REPRODUCTIVE ORGANS

A. Stamens, filaments and anthers:

1. *Stamens.*—Yellow.
2. *Anthers.*—Color — just before opening: white.
3. *Pollen.*—Yellow with white.

B. Pistils:

1. *Styles.*—Yellow.
2. *Stigmas.*—Yellow.

I claim:

1. A new and distinct variety of pot freesia substantially as described and illustrated herein.

* * * * *

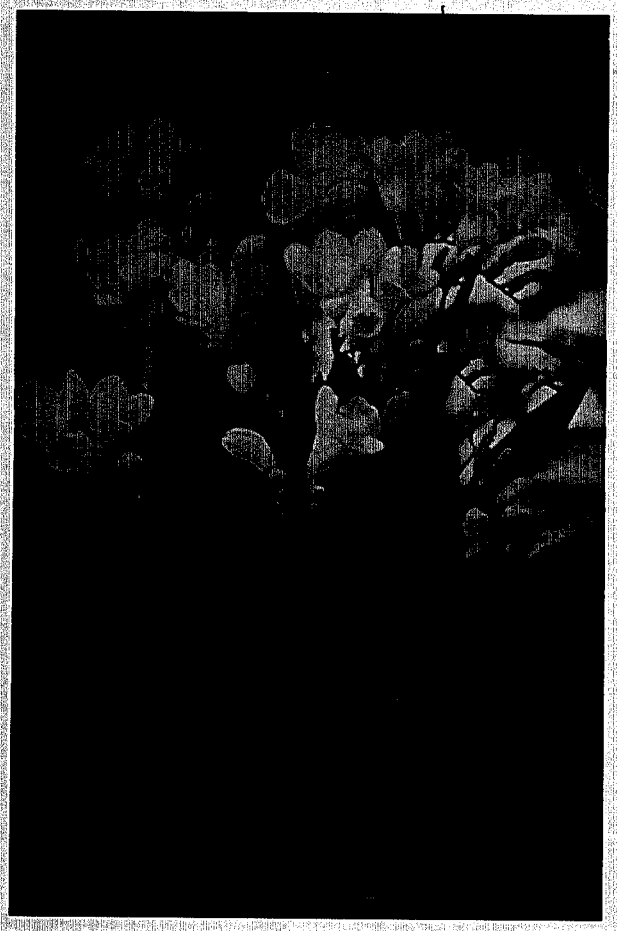

UNITED STATES PATENT AND TRADEMARK OFFICE

CERTIFICATE OF CORRECTION

PATENT NO. : Plant 9,296

DATED : September 19, 1995

INVENTOR(S) : Jacob van Andel

It is certified that error appears in the above-indentified patent and that said Letters Patent is hereby corrected as shown below:

Column 2, line 28, change "6. *Veination*.13 Freesia-like." to -- 6. *Veination*.—Freesia-like --.

Column 4, line 3, change "5. *Petals*.13 Number of petals:" to -- 5. *Petals*.—Number of petals. --.

Signed and Sealed this

Second Day of April, 1996

*Attest:*

*Attesting Officer*

BRUCE LEHMAN

*Commissioner of Patents and Trademarks*